United States Patent
Radspinner et al.

(10) Patent No.: US 12,364,603 B2
(45) Date of Patent: Jul. 22, 2025

(54) IMPLANTABLE COMPONENT WITH SOCKET

(71) Applicant: W. L. Gore & Associates, Inc., Newark, DE (US)

(72) Inventors: Rachel Radspinner, Flagstaff, AZ (US); Ian Smith, Flagstaff, AZ (US); Patrick S. Young, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 18/144,631

(22) Filed: May 8, 2023

(65) Prior Publication Data

US 2023/0270548 A1  Aug. 31, 2023

Related U.S. Application Data

(63) Continuation of application No. 16/710,637, filed on Dec. 11, 2019, now Pat. No. 11,678,983.

(Continued)

(51) Int. Cl.
*A61F 2/24* (2006.01)
*A61M 60/178* (2021.01)
*A61M 60/237* (2021.01)
*A61M 60/861* (2021.01)
*A61F 2/00* (2006.01)

(52) U.S. Cl.
CPC ......... *A61F 2/2457* (2013.01); *A61M 60/178* (2021.01); *A61M 60/237* (2021.01); *A61M 60/861* (2021.01); *A61F 2002/0086* (2013.01); *A61F 2220/0016* (2013.01); *A61F 2220/0033* (2013.01); *A61F 2230/0091* (2013.01); *A61M 2205/04* (2013.01)

(58) Field of Classification Search
CPC ............ A61F 2/2457; A61F 2220/0033; A61F 2220/0016; A61F 2002/0086; A61F 2230/0091; A61M 2205/04
See application file for complete search history.

(56) References Cited

U.S. PATENT DOCUMENTS 3,618,604 A  11/1971  Ness
3,683,928 A  8/1972  Kuntz
(Continued)

FOREIGN PATENT DOCUMENTS

AU  06600/12 B2  6/1995
CA  2502761 A1  4/1997
(Continued)

OTHER PUBLICATIONS

Ando et al., Ten-year experience with handmade trileaflet polytetrafluoroethylene valved conduit used for pulmonary reconstruction. The Journal of Thoracic and Cardiovascular Surgery, Jan. 2009, vol. 137, No. 1, pp. 124-131.
(Continued)

*Primary Examiner* — Dinah Baria

(57) ABSTRACT

Implantable devices may include a single, first component or a plurality of components such as first and second components, the second component being flexibly coupled to the first component. A socket extends over one or more of the component(s), the socket being configured to enhance the inter-component interaction and/or including one or more exposed surface(s) configured to exhibit one or more tiers of foreign body responses within a range of possible foreign body responses.

16 Claims, 12 Drawing Sheets

Related U.S. Application Data

(60) Provisional application No. 62/778,654, filed on Dec. 12, 2018.

(56) References Cited

U.S. PATENT DOCUMENTS

| | | |
|---|---|---|
| 3,828,777 A | 8/1974 | Ness |
| 3,960,150 A | 6/1976 | Hussain et al. |
| 3,962,414 A | 6/1976 | Michaels |
| 4,014,335 A | 3/1977 | Arnold |
| 4,182,342 A | 1/1980 | Smith |
| 4,214,586 A | 7/1980 | Mericle |
| 4,579,221 A | 4/1986 | Corella |
| 4,759,759 A | 7/1988 | Walker et al. |
| 5,037,434 A | 8/1991 | Lane |
| 5,080,676 A | 1/1992 | May |
| 5,147,647 A | 9/1992 | Darougar |
| 5,163,955 A | 11/1992 | Love et al. |
| 5,282,851 A | 2/1994 | Jacob-LaBarre |
| 5,378,475 A | 1/1995 | Smith et al. |
| 5,423,777 A | 6/1995 | Tajiri et al. |
| 5,681,275 A | 10/1997 | Ahmed |
| 5,702,414 A | 12/1997 | Richter et al. |
| 5,708,044 A | 1/1998 | Branca |
| 5,713,953 A | 2/1998 | Vallana et al. |
| 5,773,019 A | 6/1998 | Ashton et al. |
| 5,861,028 A | 1/1999 | Angell |
| 5,882,327 A | 3/1999 | Jacob |
| 5,928,281 A | 7/1999 | Huynh et al. |
| 5,935,163 A | 8/1999 | Gabbay |
| 6,074,419 A | 6/2000 | Healy et al. |
| 6,086,612 A | 7/2000 | Jansen |
| 6,142,969 A | 11/2000 | Nigam |
| 6,171,335 B1 | 1/2001 | Wheatley et al. |
| 6,174,331 B1 | 1/2001 | Moe et al. |
| 6,197,143 B1 | 3/2001 | Bodnar |
| 6,254,636 B1 | 7/2001 | Peredo |
| 6,283,995 B1 | 9/2001 | Moe et al. |
| 6,287,338 B1 | 9/2001 | Sarnowski et al. |
| 6,364,905 B1 | 4/2002 | Simpson et al. |
| 6,432,542 B1 | 8/2002 | Tsai |
| 6,450,984 B1 | 9/2002 | Lynch et al. |
| 6,471,689 B1 | 10/2002 | Joseph et al. |
| 6,541,589 B1 | 4/2003 | Baillie |
| 6,562,069 B2 | 5/2003 | Cai et al. |
| 6,613,086 B1 | 9/2003 | Moe et al. |
| 6,613,087 B1 | 9/2003 | Healy et al. |
| 6,696,526 B1 | 2/2004 | Kaulbach et al. |
| 6,699,210 B2 | 3/2004 | Williams et al. |
| 6,699,211 B2 | 3/2004 | Savage |
| 6,713,081 B2 | 3/2004 | Robinson et al. |
| 6,994,666 B2 | 2/2006 | Shannon et al. |
| 7,018,404 B2 | 3/2006 | Holmberg et al. |
| 7,261,732 B2 | 8/2007 | Justino |
| 7,306,729 B2 | 12/2007 | Bacino et al. |
| 7,320,705 B2 | 1/2008 | Quintessenza |
| 7,331,993 B2 | 2/2008 | White |
| 7,361,189 B2 | 4/2008 | Case et al. |
| 7,462,675 B2 | 12/2008 | Chang et al. |
| 7,531,611 B2 | 5/2009 | Sabol et al. |
| 7,604,663 B1 | 10/2009 | Reimink et al. |
| 7,833,565 B2 | 11/2010 | O'Connor et al. |
| 7,862,610 B2 | 1/2011 | Quintessenza |
| 8,216,631 B2 | 7/2012 | O'Connor et al. |
| 8,219,229 B2 | 7/2012 | Cao et al. |
| 8,246,676 B2 | 8/2012 | Acosta et al. |
| 8,267,994 B2 | 9/2012 | Jin |
| 8,273,101 B2 | 9/2012 | Garcia et al. |
| 8,303,647 B2 | 11/2012 | Case |
| 8,399,006 B2 | 3/2013 | De et al. |
| 8,545,430 B2 | 10/2013 | Silvestrini |
| 8,556,960 B2 | 10/2013 | Agnew et al. |
| 8,623,395 B2 | 1/2014 | De et al. |
| 8,632,489 B1 | 1/2014 | Ahmed |
| 8,637,144 B2 | 1/2014 | Ford |
| 8,690,939 B2 | 4/2014 | Miller |
| 8,834,406 B2 | 9/2014 | Snyder et al. |
| 8,834,911 B2 | 9/2014 | Glezer et al. |
| 8,961,593 B2 | 2/2015 | Bonhoeffer et al. |
| 8,961,599 B2 | 2/2015 | Bruchman et al. |
| 8,961,600 B2 | 2/2015 | Nissan et al. |
| 9,139,669 B2 | 9/2015 | Xu et al. |
| 9,155,610 B2 | 10/2015 | Soletti et al. |
| 9,155,618 B2 | 10/2015 | Kalmann et al. |
| 9,259,313 B2 | 2/2016 | Wheatley |
| 9,301,835 B2 | 4/2016 | Campbell et al. |
| 9,301,837 B2 | 4/2016 | Beith |
| 9,326,891 B2 | 5/2016 | Horvath et al. |
| 9,364,322 B2 | 6/2016 | Conklin et al. |
| 9,370,444 B2 | 6/2016 | Cunningham, Jr. |
| 9,539,089 B2 | 1/2017 | Beith |
| 9,572,713 B2 | 2/2017 | Lind et al. |
| 9,636,219 B2 | 5/2017 | Keidar et al. |
| 9,636,254 B2 | 5/2017 | Yu et al. |
| 9,655,720 B2 | 5/2017 | Bluestein et al. |
| 9,675,453 B2 | 6/2017 | Guttenberg et al. |
| 9,833,314 B2 | 12/2017 | Corbett |
| 9,849,629 B2 | 12/2017 | Zaggl et al. |
| 9,877,833 B1 | 1/2018 | Bishop et al. |
| 9,987,120 B2 | 6/2018 | Soletti et al. |
| 9,999,500 B2 | 6/2018 | Greenslet et al. |
| 10,052,200 B2 | 8/2018 | Chung et al. |
| 10,195,023 B2 | 2/2019 | Wrobel |
| 10,299,915 B2 | 5/2019 | Edelman et al. |
| 10,307,292 B2 | 6/2019 | Litvin |
| 10,413,402 B2 | 9/2019 | Squara |
| 10,413,403 B2 | 9/2019 | Boden et al. |
| 10,426,609 B2 | 10/2019 | Edelman et al. |
| 10,433,955 B2 | 10/2019 | Edelman et al. |
| 10,512,537 B2 | 12/2019 | Corbett et al. |
| 10,588,746 B2 | 3/2020 | Bernstein et al. |
| 10,603,164 B2 | 3/2020 | Girard et al. |
| 11,351,058 B2 | 6/2022 | Roeber et al. |
| 11,678,983 B2 | 6/2023 | Radspinner et al. |
| 2002/0106395 A1 | 8/2002 | Brubaker |
| 2002/0110635 A1 | 8/2002 | Brubaker et al. |
| 2002/0156413 A1 | 10/2002 | Williams et al. |
| 2002/0198594 A1 | 12/2002 | Schreck |
| 2003/0027332 A1 | 2/2003 | Lafrance et al. |
| 2003/0088260 A1 | 5/2003 | Smedley et al. |
| 2003/0094731 A1 | 5/2003 | Simpson |
| 2003/0109923 A1 | 6/2003 | Chinn et al. |
| 2004/0024345 A1 | 2/2004 | Gharib et al. |
| 2004/0215333 A1 | 10/2004 | Duran et al. |
| 2005/0085892 A1 | 4/2005 | Goto et al. |
| 2005/0137538 A1 | 6/2005 | Kunzler et al. |
| 2005/0137614 A1 | 6/2005 | Porter et al. |
| 2005/0171507 A1 | 8/2005 | Christian et al. |
| 2005/0182350 A1 | 8/2005 | Nigam |
| 2005/0228487 A1 | 10/2005 | Kujawski |
| 2005/0234546 A1 | 10/2005 | Nugent et al. |
| 2005/0261759 A1 | 11/2005 | Lambrecht et al. |
| 2005/0266047 A1 | 12/2005 | Tu et al. |
| 2005/0273033 A1 | 12/2005 | Grahn et al. |
| 2006/0109923 A1 | 5/2006 | Cai et al. |
| 2006/0110429 A1 | 5/2006 | Reiff et al. |
| 2006/0189917 A1 | 8/2006 | Mayr et al. |
| 2006/0195187 A1 | 8/2006 | Stegmann et al. |
| 2006/0258994 A1 | 11/2006 | Avery |
| 2007/0078371 A1 | 4/2007 | Brown et al. |
| 2007/0083184 A1 | 4/2007 | Simpson |
| 2007/0088432 A1 | 4/2007 | Solovay et al. |
| 2007/0118147 A1 | 5/2007 | Smedley et al. |
| 2007/0293872 A1 | 12/2007 | Peyman |
| 2008/0071361 A1 | 3/2008 | Tuval et al. |
| 2008/0082161 A1 | 4/2008 | Woo |
| 2008/0091261 A1 | 4/2008 | Long et al. |
| 2008/0133005 A1 | 6/2008 | Andrieu et al. |
| 2008/0200977 A1 | 8/2008 | Paul et al. |
| 2008/0264993 A1 | 10/2008 | Schulte et al. |
| 2008/0312737 A1 | 12/2008 | Jin |
| 2009/0157175 A1 | 6/2009 | Benichou |
| 2009/0240320 A1 | 9/2009 | Tuval et al. |
| 2009/0299469 A1 | 12/2009 | Kollar |
| 2010/0015200 A1 | 1/2010 | McClain et al. |

(56) References Cited

U.S. PATENT DOCUMENTS

| | | |
|---|---|---|
| 2010/0023117 A1 | 1/2010 | Yoganathan et al. |
| 2010/0082094 A1 | 4/2010 | Quadri et al. |
| 2010/0114307 A1 | 5/2010 | Agnew et al. |
| 2010/0114309 A1 | 5/2010 | De et al. |
| 2010/0119580 A1 | 5/2010 | Guo et al. |
| 2010/0137981 A1 | 6/2010 | Silvestrini et al. |
| 2010/0161040 A1 | 6/2010 | Braido et al. |
| 2010/0168644 A1 | 7/2010 | Brown |
| 2010/0168839 A1 | 7/2010 | Braido et al. |
| 2010/0185277 A1 | 7/2010 | Braido et al. |
| 2010/0241046 A1 | 9/2010 | Pinchuk et al. |
| 2011/0112620 A1 | 5/2011 | Du |
| 2011/0196487 A1 | 8/2011 | Badawi et al. |
| 2011/0244014 A1 | 10/2011 | Williams et al. |
| 2011/0257738 A1 | 10/2011 | Corbett et al. |
| 2011/0270388 A9 | 11/2011 | Stevens |
| 2011/0276128 A1 | 11/2011 | Cao et al. |
| 2011/0282440 A1 | 11/2011 | Cao et al. |
| 2011/0288635 A1 | 11/2011 | Miller et al. |
| 2012/0035525 A1 | 2/2012 | Silvestrini |
| 2012/0123315 A1 | 5/2012 | Horvath et al. |
| 2012/0123317 A1 | 5/2012 | Horvath et al. |
| 2012/0165720 A1 | 6/2012 | Horvath et al. |
| 2012/0197175 A1 | 8/2012 | Horvath et al. |
| 2012/0253453 A1 | 10/2012 | Bruchman et al. |
| 2012/0310137 A1 | 12/2012 | Silvestrini |
| 2012/0323315 A1 | 12/2012 | Bruchman et al. |
| 2013/0046379 A1 | 2/2013 | Paolitto et al. |
| 2013/0211314 A1 | 8/2013 | Venkatraman et al. |
| 2013/0218081 A1 | 8/2013 | Roth |
| 2013/0231733 A1 | 9/2013 | Knisley et al. |
| 2013/0274691 A1 | 10/2013 | De et al. |
| 2013/0325024 A1 | 12/2013 | Nissan et al. |
| 2013/0325111 A1 | 12/2013 | Campbell et al. |
| 2014/0012371 A1 | 1/2014 | Li |
| 2014/0031927 A1 | 1/2014 | Bruchman et al. |
| 2014/0128960 A1 | 5/2014 | Greenslet et al. |
| 2014/0154321 A1 | 6/2014 | Ashton |
| 2014/0170204 A1 | 6/2014 | Desai et al. |
| 2014/0186420 A1 | 7/2014 | Utkhede et al. |
| 2014/0214158 A1 | 7/2014 | Board et al. |
| 2014/0236067 A1 | 8/2014 | Horvath et al. |
| 2014/0236068 A1 | 8/2014 | Van et al. |
| 2014/0358224 A1 | 12/2014 | Tegels et al. |
| 2015/0005689 A1 | 1/2015 | Horvath et al. |
| 2015/0119980 A1 | 4/2015 | Beith et al. |
| 2015/0216662 A1 | 8/2015 | Medema et al. |
| 2015/0224200 A1 | 8/2015 | De et al. |
| 2015/0224231 A1 | 8/2015 | Bruchman et al. |
| 2015/0320975 A1 | 11/2015 | Simpson et al. |
| 2015/0374545 A1 | 12/2015 | Horvath et al. |
| 2016/0015516 A1 | 1/2016 | Bernstein et al. |
| 2016/0038412 A1 | 2/2016 | Guo et al. |
| 2016/0058616 A1 | 3/2016 | Camras et al. |
| 2016/0067032 A1 | 3/2016 | Soletti et al. |
| 2016/0100939 A1 | 4/2016 | Armstrong et al. |
| 2016/0153591 A1 | 6/2016 | Fonfara et al. |
| 2016/0245432 A1 | 8/2016 | Fonfara et al. |
| 2016/0256321 A1 | 9/2016 | Horvath et al. |
| 2016/0256382 A1 | 9/2016 | Shi et al. |
| 2016/0287513 A1 | 10/2016 | Rakic et al. |
| 2016/0296322 A1 | 10/2016 | Edelman et al. |
| 2016/0302965 A1 | 10/2016 | Erickson et al. |
| 2016/0302967 A1 | 10/2016 | Ahn |
| 2016/0331528 A1 | 11/2016 | Parker et al. |
| 2016/0374856 A1 | 12/2016 | Pinchuk et al. |
| 2017/0000610 A1 | 1/2017 | Eppihimer et al. |
| 2017/0014227 A1 | 1/2017 | Boden et al. |
| 2017/0071729 A1 | 3/2017 | Wrobel |
| 2017/0079779 A1 | 3/2017 | Tabor |
| 2017/0079782 A1 | 3/2017 | Beith |
| 2017/0156854 A1 | 6/2017 | Hammer |
| 2017/0172794 A1 | 6/2017 | Varner et al. |
| 2017/0189175 A1 | 7/2017 | Justino et al. |
| 2017/0245989 A1 | 8/2017 | Bluestein et al. |
| 2017/0252156 A1 | 9/2017 | Bernstein et al. |
| 2017/0296783 A1 | 10/2017 | Connolly et al. |
| 2017/0367888 A1 | 12/2017 | Brown |
| 2018/0049872 A1 | 2/2018 | Bennett |
| 2018/0125632 A1 | 5/2018 | Cully et al. |
| 2018/0133002 A1 | 5/2018 | Yi et al. |
| 2018/0177592 A1 | 6/2018 | Benichou et al. |
| 2018/0185151 A1 | 7/2018 | Bishop |
| 2018/0263775 A1 | 9/2018 | Shah |
| 2018/0263817 A1 | 9/2018 | Roeber et al. |
| 2018/0263818 A1 | 9/2018 | Roeber et al. |
| 2018/0263819 A1 | 9/2018 | Roeber et al. |
| 2018/0344457 A1 | 12/2018 | Gross et al. |
| 2019/0015191 A1 | 1/2019 | Berdajs |
| 2019/0091014 A1 | 3/2019 | Arcaro et al. |
| 2019/0091015 A1 | 3/2019 | Dienno et al. |
| 2019/0125529 A1 | 5/2019 | Colavito et al. |
| 2019/0125530 A1 | 5/2019 | Arcaro et al. |
| 2019/0125531 A1 | 5/2019 | Bennett et al. |
| 2019/0282360 A1 | 9/2019 | Colavito et al. |
| 2019/0282364 A1 | 9/2019 | Khairkhahan et al. |
| 2019/0343617 A1 | 11/2019 | Sobrino-Serrano et al. |
| 2019/0365531 A1 | 12/2019 | Beith |
| 2020/0113681 A1 | 4/2020 | Armstrong et al. |
| 2020/0121454 A1 | 4/2020 | Spence |
| 2020/0188114 A1 | 6/2020 | Radspinner et al. |
| 2021/0322217 A1 | 10/2021 | Roeber et al. |
| 2021/0346197 A1 | 11/2021 | Roeber et al. |

FOREIGN PATENT DOCUMENTS

| | | |
|---|---|---|
| CN | 1208602 A | 2/1999 |
| CN | 2414757 Y | 1/2001 |
| CN | 1285724 A | 2/2001 |
| CN | 101965211 A | 2/2011 |
| CN | 103179927 A | 6/2013 |
| CN | 104203300 A | 12/2014 |
| CN | 105579001 A | 5/2016 |
| CN | 205198254 U | 5/2016 |
| EP | 0368488 A1 | 5/1990 |
| EP | 2349147 B1 | 3/2015 |
| EP | 2958530 A1 | 12/2015 |
| GB | 2513194 A | 10/2014 |
| IN | 202619978 U | 12/2012 |
| JP | 08-117267 A | 5/1996 |
| JP | 11-505159 A | 5/1999 |
| JP | 2000-513248 A | 10/2000 |
| JP | 2002-521145 A | 7/2002 |
| JP | 2003-301948 A | 10/2003 |
| JP | 2005-500101 A | 1/2005 |
| JP | 2007-521125 | 8/2007 |
| JP | 2010-540079 A | 12/2010 |
| JP | 2012-504031 A | 2/2012 |
| JP | 2013-009982 A | 1/2013 |
| JP | 2014-517720 A | 7/2014 |
| JP | 2016-137278 A | 8/2016 |
| JP | 2016-533798 A | 11/2016 |
| WO | 2001/066037 A2 | 9/2001 |
| WO | 2003/007795 A2 | 1/2003 |
| WO | 2005/076973 A2 | 8/2005 |
| WO | 2007/100408 A2 | 9/2007 |
| WO | 2008/030951 A2 | 3/2008 |
| WO | 2008/133852 A1 | 11/2008 |
| WO | 2009/042196 A2 | 4/2009 |
| WO | 2009/137785 A2 | 11/2009 |
| WO | 2010/037141 A1 | 4/2010 |
| WO | 2011/147849 A1 | 12/2011 |
| WO | 2012/018779 A2 | 2/2012 |
| WO | 2012/094641 A2 | 7/2012 |
| WO | 2012/135603 A2 | 10/2012 |
| WO | 2013/090006 A1 | 6/2013 |
| WO | 2013/096854 A3 | 8/2013 |
| WO | 2014/028725 A1 | 2/2014 |
| WO | 2014/130574 A1 | 8/2014 |
| WO | 2014/145811 A1 | 9/2014 |
| WO | 2015/065646 A1 | 5/2015 |
| WO | 2016/033270 A1 | 3/2016 |
| WO | 2016/168686 A1 | 10/2016 |
| WO | 2016/196841 A1 | 12/2016 |

(56) References Cited

FOREIGN PATENT DOCUMENTS

| WO | 2018/150392 A1 | 8/2018 |
|---|---|---|
| WO | 2018/169878 A1 | 9/2018 |
| WO | 2018/170429 A1 | 9/2018 |
| WO | 2018/170433 A1 | 9/2018 |
| WO | 2018/187714 A1 | 10/2018 |
| WO | 2019/154927 A1 | 8/2019 |

OTHER PUBLICATIONS

Gedde et al., "Treatment Outcomes in the Tube Versus Trabeculectomy (TVT) Study After Five Years of Follow-up", Am J Ophthalmol., vol. 153, No. 5, 2012, pp. 789-803.
Han, et al. "Membrane-tube-type glaucoma shunt device for refractory glaucoma surgery", Glaucoma, Graefes Arch Clin Exp Opthalmol, DOI 10, 1007/s00417-016-3510-z. Springer-Verlag Berlin Heidelberg 2016.
International Preliminary Report on Patentability received for PCT Patent Application No. PCT/US2019/065890, mailed on Jun. 24, 2021, 8 pages.
International Search Report and Written Opinion received for PCT Patent Application No. PCT/US2019/065890, mailed on Mar. 18, 2020, 9 pages.
Karthikeyan et al., "The concept of ocular inserts as drug delivery systems: An overview", Asian Journal Of Pharmaceutics, vol. 2, No. 4, 2008, pp. 192-200.
Lee et al., "Aqueous-Venous Shunt for Glaucoma A Further Report", Arch Opthalmol, vol. 99, 1981, pp. 2007-2012.
Lee et al., "Aqueous-Venous Shunt in The Rabbit Eye: A Long-Term Follow-Up", Trans. Soc. Ophthal. Sin., vol. 8, 1969, pp. 7-24.
Lee et al., "Aqueous-Venus Shunt for Glaucoma: Report on 15 cases", AnnalOphthal, Oct. 1974, pp. 1083-1088.
Lee et al., "Effect of an Aqueous-Venous Shunt In The Monkey Eye", Canad. J. Ophthal., 3:22, 1968, pp. 22-27.
Lee et al., "Effect of aqueous-venous shunt on rabbit eyes", Inivestigative Ophthalmology, vol. 5, No. 3, 1996, pp. 304-311.
Lee et al., "Glaucoma Microsurgery Aqueous-Venous Shunt Procedure", International Surgery, vol. 57, No. 1, Jan. 1972, pp. 37-41.
Miyazaki, et al., Expanded polytetrafluoroethylene conduits and patches with bulging sinuses and fan-shaped valves in right ventricular outflow tract reconstruction: Multicneter study in Japan. The Journal of Thoracic and Cardiovascular Surgery, Nov. 2011, vol. 142, No. 5, pp. 1122-1129.
Miyazaki, et al., Expanded polytetrafluoroethylene valved conduit and patch with bulging sinuses in right ventricular outflow tract reconstruction. The Journal of Thoracic and Cardiovascular Surgery, Aug. 2007, vol. 134, No. 2, pp. 327-332.
Ootaki et al., Medium-term outcomes after implantation of expanded polytetrafluoroethylene valved conduit. The Annals of Thoracic Surgery, 2018; 105 (3), pp. 843-850.
Rese et al., "Sustained drug delivery in glaucoma", Current Opinion in Ophthalmology, vol. 25, No. 2, 2014, pp. 112-117.
Shinkawa et al., Valved polytetrafluoroethylene conduits for right ventricular outflow tract reconstruction. The Annals of Thoracic Surgery. Jul. 2015; 100(1), pp. 129-137.
Stevenson et al., "Reservoir-Based Drug Delivery Systems Utilizing Microtechnology", Advanced Drug Delivery Reviews, vol. 64, No. 14, 2012, pp. 1590-1602.
Understanding Your Heart Valve. Medtronic USA, Inc., 2006. Pamphlet.
Yamagishi et al. Outflow reconstruction of tetralogy of fallot using a Gore-Tex valve. The Anais of Thoracic Surgery, Dec. 1993; 56(6), pp. 1414-1417.

IMPLANTABLE COMPONENT WITH SOCKET

CROSS-REFERENCE TO RELATED APPLICATION

This application is a continuation of U.S. application Ser. No. 16/710,637, filed Dec. 11, 2019, which claims the benefit of Provisional Application No. 62/778,654, filed Dec. 12, 2018, which are incorporated herein by reference in its entireties for all purposes.

FIELD

The present disclosure relates generally to covers, receptacles, shrouds, couplers, constrainers and the like (collectively, sockets) for implantable medical devices, and more specifically sockets configured to enhance inter-component and/or inter-environment interactions of an implantable device.

BACKGROUND

Implantable device components are implemented in a variety of contexts, such as transcatheter mitral chordal repair devices. Improvements in the interactions between a plurality of device components in vivo, as well as interactions between the plurality of device components and the bodily environment remain to be realized.

SUMMARY

Various examples relate to an implantable medical device (e.g., a transcatheter mitral chordal device) that includes a first component (e.g., an anchor component) and a second component coupled to the first component (e.g., a tether component). Interactions (e.g., relative movement, flexing, abrading, or other mechanical interactions) between the first and second components may benefit from being controlled (e.g., minimized) and interactions between the first and/or second components and the bodily environment may be enhanced (e.g., by encouraging tissue ingrowth and/or minimizing thrombosis). In further examples, interactions between the first and/or second components and a third component (e.g., a tether lock component) are improved (e.g., by reducing relative movement and/or facilitating inter-component docking), and interactions between the third component and the bodily environment are improved (e.g., by encouraging tissue ingrowth and/or minimizing thrombosis). Various examples provided herein relate to covers, receptacles, shrouds, couplers, constrainers, retaining members and the like (collectively referred to herein as, "sockets") for enhancing such inter-component and inter-environment interactions of an implantable device.

According to a first example, ("Example 1"), an implantable device includes a first component; a second component flexibly coupled to the first component; and a socket extending over the first component and the second component, the socket being configured to enhance the inter-component interaction between the first and second components of the implantable device by reducing relative movement between the first and second components, wherein the socket includes one or more outer exposed surface(s) configured to exhibit one or more tiers of foreign body responses within a range of possible foreign body responses.

According to another example, ("Example 2"), further to Example 1, the one or more outer exposed surfaces is configured to exhibit a foreign body response including extracellular matrix integration.

According to another example, ("Example 3"), further to any preceding Example, the socket includes one or more layers of material that is impermeable to cellular integration.

According to another example, ("Example 4"), further to any preceding Example, the socket includes one or more layers of material having a microstructure that is oriented to provide longitudinal strength to one or more portions of the socket.

According to another example, ("Example 5"), further to any preceding Example, the socket includes one or more layers of material having a microstructure that is oriented to provide circumferential strength to one or more portions of the socket.

According to another example, ("Example 6"), further to any preceding Example, the socket includes one or more reinforcing rings.

According to another example, ("Example 7"), further to Example 6 at least one of the one or more reinforcing rings is elastically deformable to an enlarged diameter from which the one or more reinforcing rings elastically recovers.

According to another example, ("Example 8"), further to Examples 6 or 7, the one or more reinforcing rings defines a continuous, helical undulating pattern.

According to another example, ("Example 9"), further to any preceding Example, the socket includes an outwardly flared end.

According to another example, ("Example 10"), further to any preceding Example, the socket includes a reinforced end.

According to another example, ("Example 11"), further to any preceding Example, the first component is an anchor component and the second component is a tether component.

According to another example, ("Example 12"), further to any preceding Example, the implantable device of any preceding claim, further comprising a third component and fourth component, the socket being configured to receive the third and fourth components to enhance the inter-component interaction between the first and third components of the implantable device.

According to another example, ("Example 13"), further to Example 12, the third component is a tether lock component and the fourth component is a tether component.

According to another example, ("Example 14"), further to any preceding Example, at least one of an outer and an inner surface of the socket includes material configured to promote tissue ingrowth.

According to another example, ("Example 15"), further to any preceding Example, the socket is formed of one or more layers of material including a film microstructure in which fibrillar orientation is in a direction aligned to a longitudinal axis of socket.

According to another example, ("Example 16"), further to any preceding Example, the socket is formed from a material set including ePTFE graft material, elastomer material, other polymeric material, or a combination of two or more such materials.

According to another example, ("Example 17"), further to any preceding Example, the socket includes an ePTFE stretch graft material.

According to another example, ("Example 18"), further to any preceding Example, the socket includes material that is partially or fully bio-resorbable and/or partially or fully bio-absorbable.

According to another example, ("Example 19"), further to any preceding Example, the socket is configured to provide temporary fixation to body tissue that degrades partially or fully over time.

According to another example, ("Example 20"), further to any preceding Example, the socket includes one or more layers configured as a mesh or network of material that is adapted to enhance biocompatibility and fibrosis following implantation.

According to another example, ("Example 21"), further to Example, 20, the mesh or network of material is formed by crossing strands of material or by intermittent voids or openings in one or more layers of material.

According to another example, ("Example 22"), further to any preceding Example, the implantable device is configured as a transcatheter mitral chordal repair device or a blood pump device.

According to another example, ("Example 23"), a method of treatment using the implantable device of any preceding Example includes delivering the implantable device to a location in a body of a patient.

According to another example, ("Example 24"), further to Example 23, the method further includes inserting another component, such as the third component of Example 12, into the socket in vivo.

According to another Example ("Example 25"), an implantable device includes a first component having a first outer profile defining first radial variability along the first component and a socket extending over the first outer profile of the first component to define a second outer profile having a second radial variability that is reduced relative to the first radial variability, wherein the socket includes one or more outer exposed surfaces configured to exhibit one or more tiers of foreign body responses within a range of possible foreign body responses. Any of the features of Examples 1 to 24 may be applicable to Example 25 as appropriate.

According to another Example ("Example 26"), a socket is configured to extend over a first outer profile of a first component of an implantable device to define a second outer profile having a second radial variability that is reduced relative to a first radial variability of the first component, wherein the socket includes one or more outer exposed surfaces configured to exhibit one or more tiers of foreign body responses within a range of possible foreign body responses.

According to another Example ("Example 27"), a socket is configured to extend over a first component and a second component of an implantable device, the socket being configured to enhance the inter-component interaction between the first and second components of the implantable device by reducing relative movement between the first and second components, wherein the socket includes one or more outer exposed surfaces configured to exhibit one or more tiers of foreign body responses within a range of possible foreign body responses.

According to another Example ("Example 28"), a method includes delivering a multi-component device to a location in a body of a patient, the multi-component device including a first component having a first outer profile defining first radial variability along the first component; and a socket extending over the first outer profile of the first component to define a second outer profile having a second radial variability that is reduced relative to the first radial variability, wherein the socket includes one or more outer exposed surfaces configured to exhibit one or more tiers of foreign body responses within a range of possible foreign body responses; and inserting a third component into the socket to enhance the inter-component interaction between the first and third components of the implantable device.

According to another example ("Example 25"), further to the method of Example 24, the third component is a tether lock component.

The foregoing Examples are just that and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Any of a variety of additional or alternative features and advantages are contemplated and will become apparent with reference to the disclosure and figures that follow. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description explain the principles of the disclosure.

Figure 1:
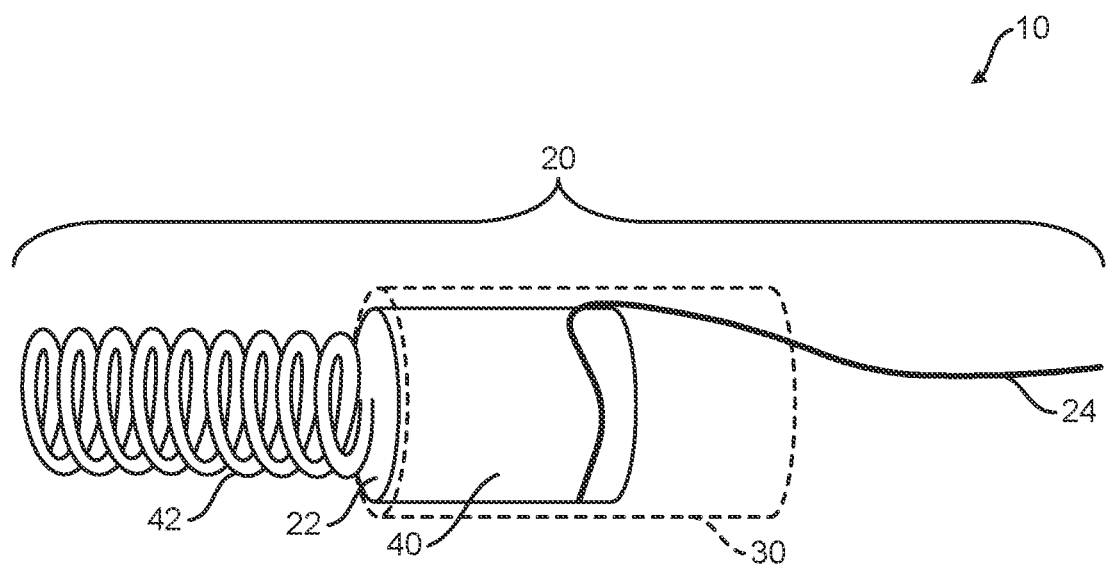
FIG. 1 shows an implantable device, according to some examples.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

The terms "substantially" and "generally" are used in the present disclosure to convey a degree of inexactitude as would be understood and readily ascertainable by a person having ordinary skill in the art.

With respect terminology of inexactitude with reference to measurements, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

As used herein, the term "tube" does not require a component with a continuous wall unless otherwise noted, but can include meshes, frameworks, perforated constructs, annular or ring constructs, and the like.

As used herein, the term "socket" is inclusive of and may be used interchangeably with any of the following terms: covers, receptacles, shrouds, couplers, constrainers, retaining members and the like.

DESCRIPTION OF VARIOUS EMBODIMENTS

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

FIG. 1 shows an implantable device 10, according to some examples. As shown, the implantable device 10 includes a plurality of components 20, such as a first component 22, a second component 24, and a socket 30 extending over the first component 22 and the second component 24. The socket 30 is generally configured to enhance inter-component and inter-environment interactions of an implantable device. For ease of illustration and visualization of the underlying components, the socket 30 is illustrated in a see-through manner, designated by broken lines. As shown, the socket 30 is generally in the form of a continuous tube, or cylinder of material although discontinuous tubes, annular tubes, and other tube variations are contemplated.

Although the implantable device 10 is subsequently described with reference to components that may be associated with a transcatheter mitral chordal repair device (e.g., such as those disclosed in U.S. Pat. App. Pub. No. 2018/0185151, "METHOD FOR TRANSVASCULAR IMPLANTATION OF NEO CHORDAE TENDINEAE,") similar principles may be applied to any of a variety of implantable devices as desired (see, e.g., FIG. 11 and associated description).

As shown, in some examples the first component 22 is configured as an anchor component having a body 40 and a barb 42. In some examples, the body component is configured to be delivered endoluminally (e.g., via transcatheter technique) and is formed of a biocompatible metal or polymeric material, for example. The barb 42 may be formed of the same, similar or different material from the body 40 and is configured to be rotated, or screwed into tissue (e.g., cardiac tissue, such as that associated with the ventricular wall of a heart). In turn, the second component 24 may be configured as a tether component formed of a relatively flexible, elongate material (e.g., monofilament, multifilament, braided, or other material). In some examples, the second component is formed of expanded polytetrafluoroethylene (ePTFE), although any of a variety of materials may be used as desired. Although the barb 42 is shown as a helical, screw type anchor, it should be understood that any of a variety of anchoring or engagement features may be substituted for the barb 42 or added in addition to the barb 42. For example, needles, arrow-shaped barbs, expanding coils or umbrella-type anchors, pledget tissue anchors, or any of a variety of other tissue anchor designs are contemplated.

As shown in FIG. 1, the second component 24 is coupled to, and extends from the first component 22. In use, the second component 24 may flex, or deflect naturally following implantation. As shown in FIG. 1, the socket 30 extends over the plurality of components 20, including the first component 22 and the second component 24. The socket 30 may extend partially over the plurality of components 20 or completely over the plurality of components 20.

As shown in FIG. 1, the socket 30 is configured to minimize flexing/deflection of the second component 24 adjacent to where the second component 24 extends from the first component 22. In particular, the socket 30 may be configured to hold the second component 24 (tether component) in position by compressing, sandwiching, guiding, and/or pressing the second component 24 close to the body 40 of the first component 22 (anchor component). By minimizing relative movement, and potential wearing/abrading/concentrated flexing at the interface between the first and second components 22, 24, the socket 30 serves to enhance the inter-component interaction between the first and second components 22, 24 of the implantable device 10.

Additionally or alternatively, as subsequently described, the socket 30 may be adapted to enhance the inter-environment interaction between the first component 22 and the second component 24 and the bodily environment (not shown). For example, the socket 30 may include one or more coatings, layers, surface treatments, or other enhancements configured to promote tissue ingrowth, inhibit tissue ingrowth, reduce thrombosis and combinations thereof in order to promote, or enhance desirable interactions between the implantable device 10 and the bodily environment in which the implantable device 10 is implanted.

Figure 2A:
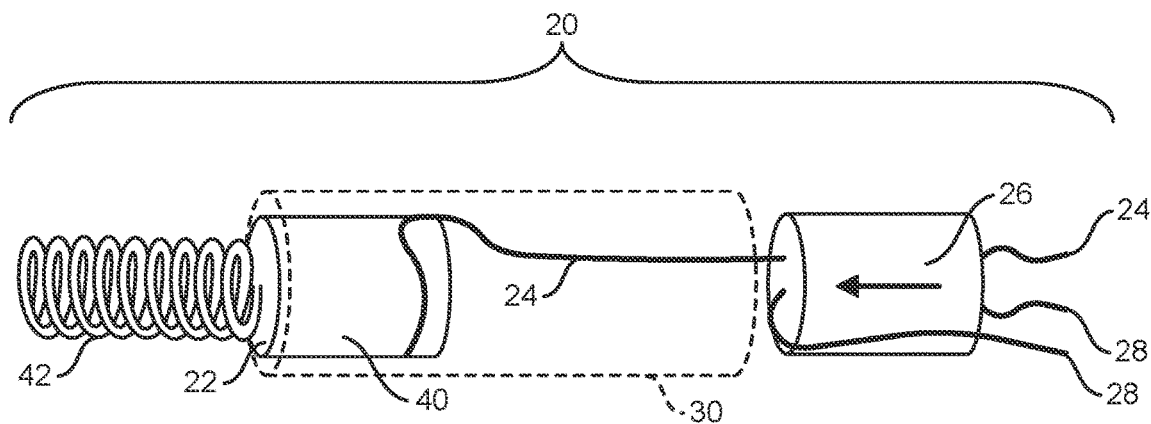
FIGS. 2A and 2B, show an implantable device, according to some examples.
Figure 2B:
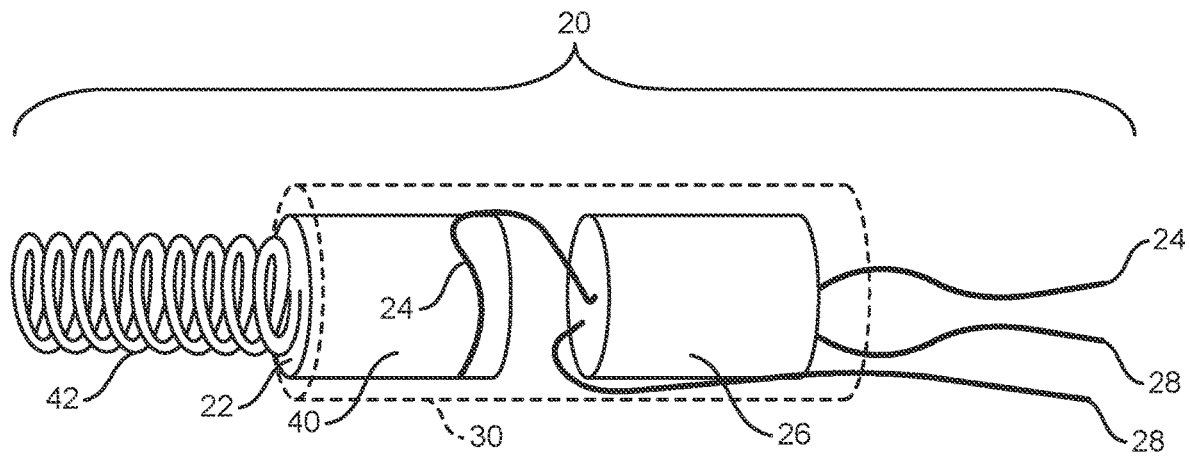

FIGS. 2A and 2B shows further, optional features of the implantable device 10. As shown, the plurality of components 20 include a third component 26 and a fourth component 28. The third component 26 may be configured as an adjustable tether lock component and the fourth component 28 may be configured as a second tether component. The third component 26 may be configured to be slid along the second component 24 (first tether component) and along the fourth component 28 (second tether component) and to lock, or arrest further sliding once positioned as desired. Examples of suitable tether lock components are desired in the previously mentioned U.S. Pat. App. Pub. No. 2018/0185151, "METHOD FOR TRANSVASCULAR IMPLANTATION OF NEO CHORDAE TENDINEAE," although any of a variety of configurations are contemplated. As shown in FIGS. 2A and 2B, the third component 26 is configured to be longitudinally slide into the socket 30 as part of delivery of the implantable device 10.

As shown in FIG. 2B, the socket 30 is configured to minimize flexing/deflection of the second component 24 adjacent to where the second component 24 extends from the first component 22 as previously described. Additionally, the socket 30 may be configured to similarly help minimize flexing between the third component (tether lock) and fourth component (second tether component) by sandwiching one or more portions of the fourth component 28 against the third component 26. Moreover, the socket 30 may assist with reducing relative movement (e.g., flexing and/or longitudinal movement) between the first component 22 (anchor component) and the third component 26 (tether lock component). In particular, the socket 30 may be configured to hold the third component 26 in position relative to the first component 22 (e.g., generally axially aligned and longitudinally proximal and/or engaging) and reduce the amount of flexing or shifting between the two. By minimizing relative movement, and potential wearing/abrading/concentrated flexing between the plurality of components 20, the socket 30 again serves to enhance the inter-component interaction of the implantable device 10. Additionally or alternatively, as previously referenced and subsequently described in greater detail, the socket 30 may be adapted to enhance the inter-environment interaction between one or more of the plurality of components 20 and the body of a patient, or bodily environment.

FIGS. 3 to 6 are illustrative of some methods of forming the socket 30 and coupling the socket 30 to the first component 22, according to some examples.

Figure 3:
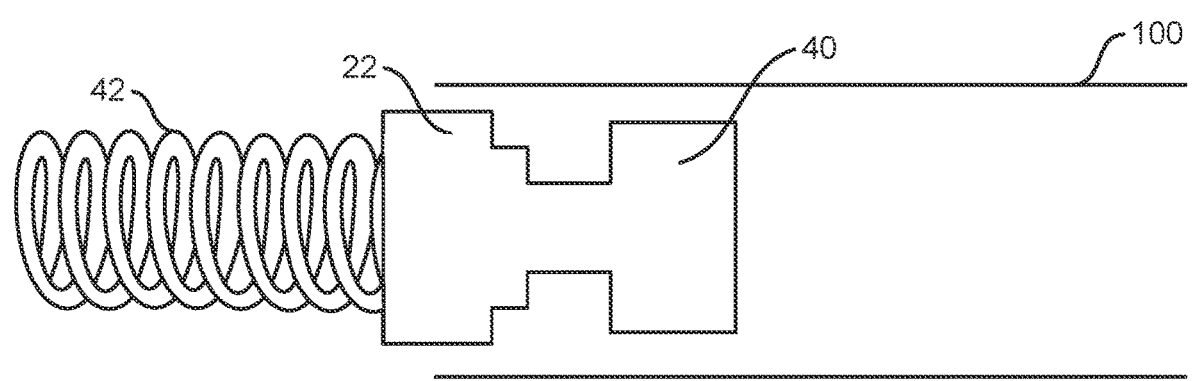
FIGS. 3 to 6 are illustrative of some methods of forming a socket and coupling the socket to a first component of an implantable device, according to some examples.

Some methods include forming a precursor tube 100 that is then formed into the socket 30. Thus, some methods of manufacture include first providing the precursor tube 100. The precursor tube 100 may be formed using wrapping techniques (e.g., tape material that is helically wrapped onto a mandrel to form the precursor tube 100 and/or sheet material that is cigarette wrapped onto a mandrel), extrusion techniques, molding techniques, combinations thereof, or other manufacturing techniques as desired. The precursor tube may be formed as a monolayer or multi-layer construct as desired. The precursor tube 100 may be formed of any of a variety of materials using any of a variety of methods, including any of those previously described. In one example, the precursor tube 100 includes one or more layers of fluoropolymer (e.g., ePTFE) material. The precursor tube 100 may generally be in the form of a hollow right cylinder, may include tapers or steps, or may have any of a variety of additional or alternative features. As shown in FIG. 3, the precursor tube 100 is generally elongate, defines a length, and includes an open inner lumen into which the first component 22 may be received.

Figure 4:
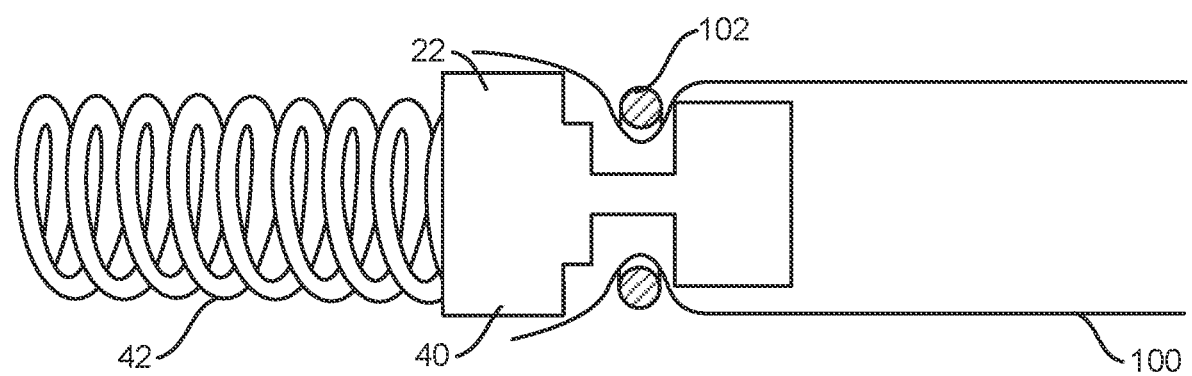

Some methods of forming the socket 30 and coupling the socket 30 to the first component 22 can be understood with reference starting at FIG. 3. As shown in FIG. 3, the precursor tube 100 is received over the body 40 of the first component 22. Then, as shown in FIG. 4, a retainer 102 may be received over the precursor tube and the body 40, with the retain 102 received in a complementary feature (e.g., a recess) formed into the body 40. The retainer 102 may be a ring or wrap of material. In some examples, the retainer 102 may be formed as a continuous ring, or partial ring of fluorinated ethylene propylene (FEP), although a variety of materials and physical configurations are contemplated.

Figure 5:
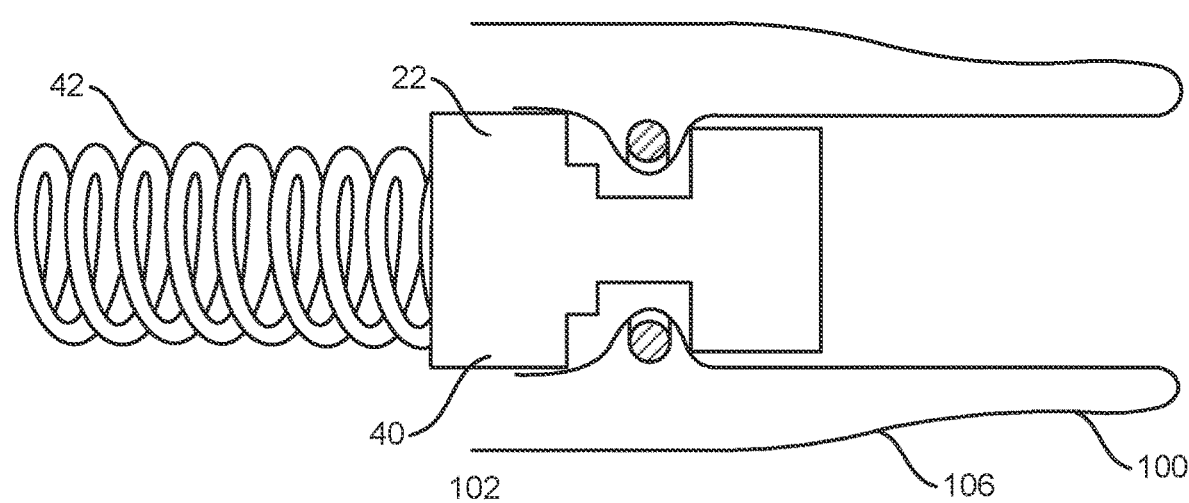

As shown in FIG. 5, one end of the precursor tube 100 may be folded back over onto itself, such that the precursor tube 100 is everted. The everted, precursor tube 100 is then doubled over, forming an inner portion 104 that may include one or more layers of material and an outer portion 106 that may include one or more layers of material. The outer portion overlays the inner portion with the retainer 102 received between the inner and outer portions.

Figure 6:
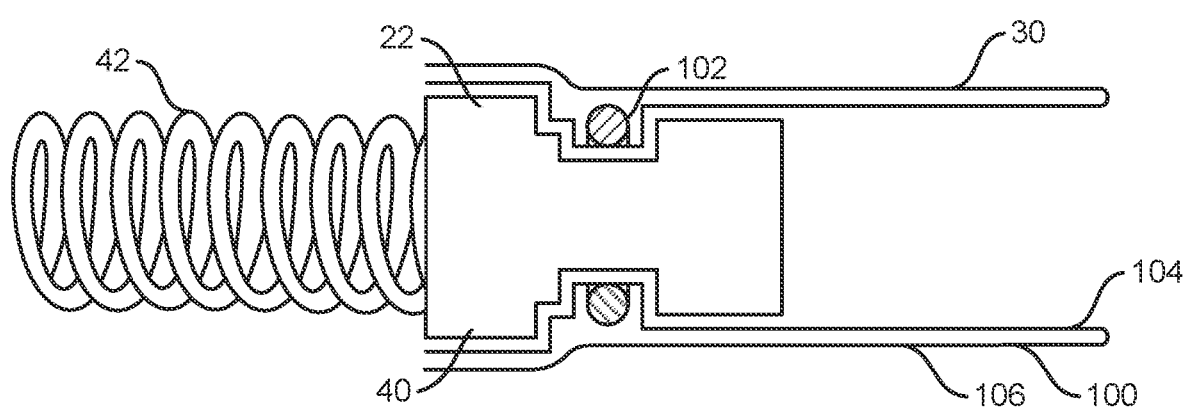

As shown in FIG. 6, the precursor tube 100 may then be bonded to itself and/or the retainer 102 (e.g., by compression, adhesion, sintering, bonding, or combinations thereof). Regardless, FIG. 6 shows the precursor tube 100 and other materials (i.e., the retainer 102) combined to form the socket 30, with the socket 30 coupled to the first component 22. In some examples, the eversion process, and formation of a double layer, helps to achieve a radially compliant structure as well as a longitudinally stiffer (e.g., relatively higher column strength) as compared to a single layer construct which helps prevent buckling of the socket 30 in examples where the third component 26 to be inserted into the socket 30 (e.g., in vivo). Radial compliance can also assist with retention of the third component 26 in the socket 30 (e.g., following insertion of the third component 26 into the socket 30).

Figure 7:
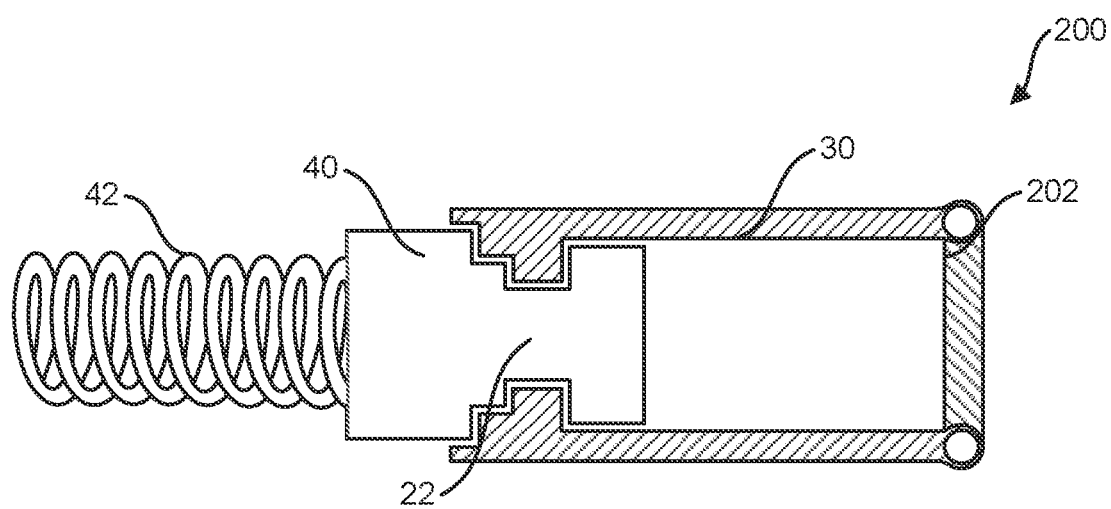
FIG. 7 shows features of a socket of an implantable device, according to some examples.

FIG. 7 shows an additional or alternative feature of the socket 30, according to some examples. For reference, formation of the socket 30 according to FIG. 7 does not require use of the manufacturing methodology described above with regard to FIGS. 3 to 6, but may certainly use such techniques as desired. Regardless, as shown in FIG. 7, the socket 30 includes an end 200 that is reinforced and/or outwardly flared which may facilitate receiving a component (e.g., the third component 26) into the socket 30. The end 200 may be reinforced and/or flared with a reinforcement member 202, such as a ring or wrap of material. In some examples, the reinforcement member 202 is a ring of material (e.g., FEP) bonded inside to, bonded outside to, or embedded in the tubular material of the socket 30. The incorporate of an outwardly flared and/or reinforced end may help ensure that the end 200 helps guide the third component 26 into the socket 30, that the end 200 remains open, and that the end 200 is robust enough to be engaged by the third component 26 without an unwanted amount of deflection, buckling, and/or folding, for example.

Figure 8:
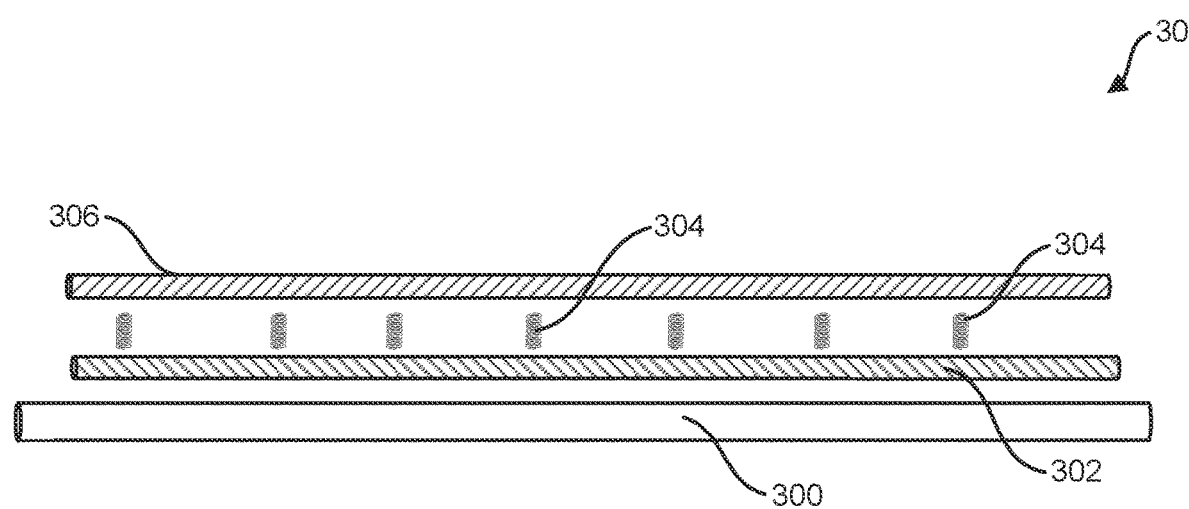
FIGS. 8 and 9 show features of a socket of an implantable device, as well as manufacturing methodology, according to some examples.
Figure 9:
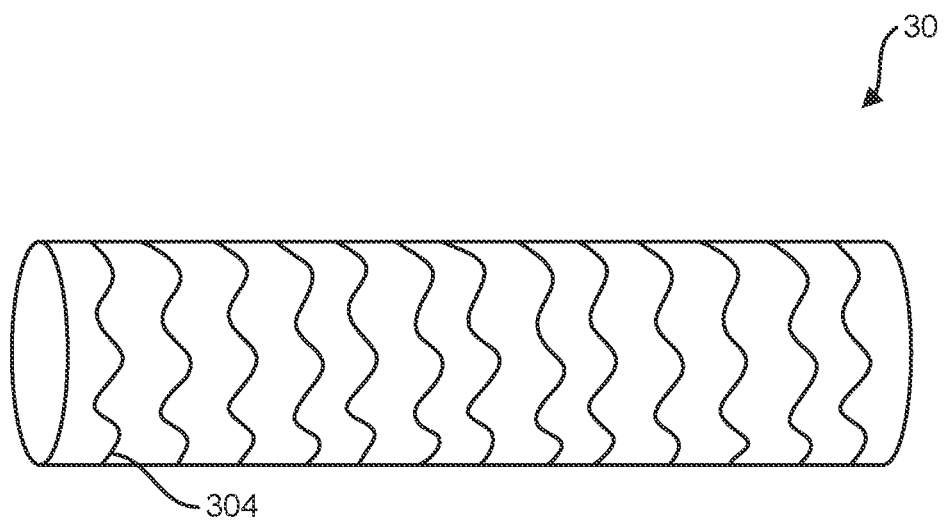

FIGS. 8 and 9 show alternative or additional features of the socket 30, as well as another manufacturing methodology which may be combined with any of the features or manufacturing techniques previously described.

As shown in FIG. 8, the socket 30 may be formed using wrapping techniques with an underlying mandrel 300 of a desired diameter. In some examples, an inner portion 302 is disposed over a mandrel 300. The inner portion 302 may be wrapped (e.g., tape wrapped), extruded, molded or otherwise formed. The inner portion 302 may include one layer or a plurality of layers as desired (e.g., or more passes, or layers of material). One or more optional reinforcing rings 304 (e.g., formed as a continuous helical structure or individual ring structures) may be applied to the inner portion 302 as desired.

The reinforcing rings 304, whether continuous (e.g., continuous helical, undulating pattern) or discontinuous (e.g., discrete, undulating pattern), may be formed of a material that is elastically deformable (e.g., distensible) such that the one or more reinforcing rings 304 will then return to its original diameter when an outer radial force is removed from the reinforcing ring(s) 304. The one or more reinforcing rings 304 can be formed of any suitable material, such as metallic materials (e.g., nitinol or stainless steel) or polymeric materials (e.g., elastomers) as desired.

As shown, an outer portion 306 may then be disposed over the inner portion 202 and the one or more reinforcing rings 304. The outer portion 306 may be wrapped (e.g., tape wrapped), extruded, molded or otherwise formed and may be one layer or a plurality of layers as desired. FIG. 9 is illustrative of an example of a completed socket 30 constructed to include the one or more reinforcing rings 304 (a plurality of reinforcing rings along the length of the socket 30 as shown).

In the examples above, the socket 30 is configured with the ability for one or more portions of the socket 30 to be expanded to an expanded diameter and then resiliently recover from such expansion. Although such examples address this feature via incorporation of elastically recoverable stent-like structure(s), the socket 30 may incorporate additional or alternative features to achieve such resilient retraction following diametric expansion. For example, materials of the socket 30 may have elastomeric materials included in one or more layers of material forming the socket 30 such that the socket 30 exhibits the ability to be diametrically distended and then elastically recover. One option includes forming one or more layers of the socket 30 of an elastomeric material (e.g., FEP). Another option would include incorporating an elastomeric material into one or more layers of the socket 30 (e.g., by coating or imbibing an expandable substrate material, such as ePTFE with an elastomeric material).

Figure 10:
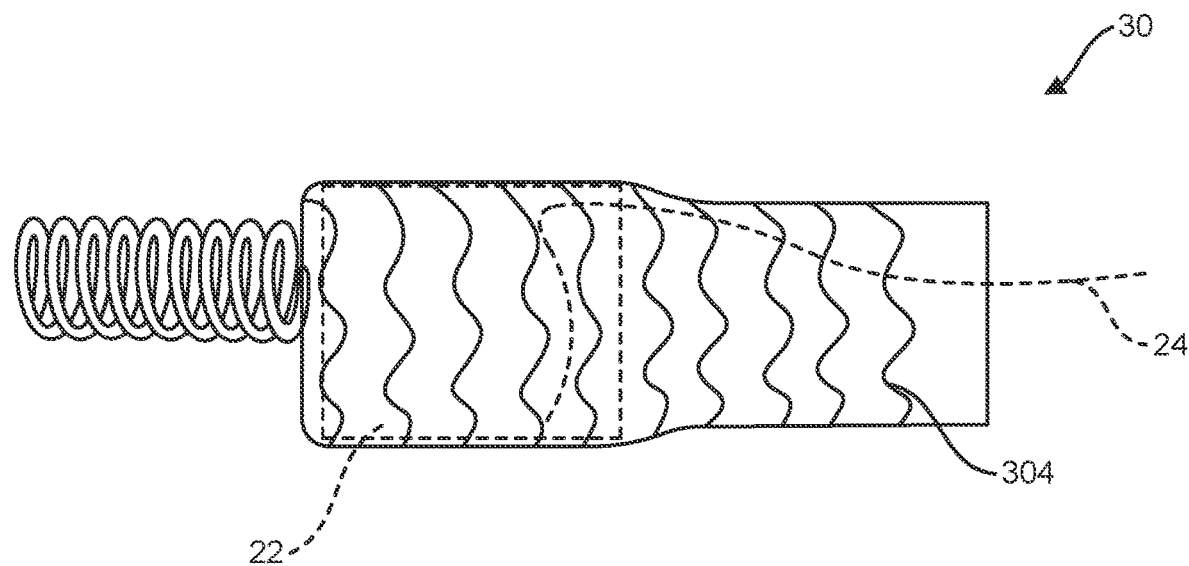
FIG. 10 shows a manner of assembling a socket to a first component of an implantable device, according to some examples.

In terms of assembly and potential advantages of incorporating elastic recovery properties, FIG. 10 is illustrative of how the socket 30 may be assembled to the first component 22 leveraging such elastic recovery properties. As shown, the socket 30 may be distended, or expanded as it is passed over the first component 22. Portions of the socket 30 on the larger diameter first component 22 then actively engage, or are biased against the first component 22. Additionally or alternatively, portions of the socket 30 that are allowed to return to a smaller diameter after being distended help retain, or secure the socket 30 to the first component. In particular, one or more portion(s) of the socket 30 neck down, or recover to a smaller diameter than adjacent portion(s) of the first component 22, thereby securing the socket 30 in place.

The materials implemented for any of the foregoing examples of the socket 30, may be configured to exhibit desired mechanical properties and/or to produce a desired response from the bodily environment. In some examples, the socket 30 includes one or more layer(s) of longitudinally-oriented material for axial, or column strength. For example, the layer(s) may include an expanded fluoropolymer with a microstructure that is oriented to provide longitudinal strength. One such material may include an expanded fluoropolymer (e.g., ePTFE) with a fibril structure that is oriented longitudinally relative to the socket 30 to enhance longitudinal, or column strength of the socket 30. The materials of the socket may also include one or more layer(s) of circumferentially-oriented material for radial, or hoop strength. For example, the socket 30 may include one or more layer(s) of circumferentially-oriented material for radial, or hoop strength. For example, the layer(s) may include an expanded fluoropolymer with a microstructure that is oriented to provide radial or hoop strength. One such material may include an expanded fluoropolymer (e.g., ePTFE) with a fibril structure that is oriented circumferentially relative to the socket 30 to enhance radial or hoop strength of the socket 30. Additionally or alternatively, such layer(s) may be combined, or may include multiple orientations (e.g., both longitudinal and circumferential) in order to achieve desired characteristics.

Additionally or alternatively, the microstructure of one or more interior or exterior layer(s) may be oriented to promote wear and abrasion resistance. For example, where abrasion is likely to be encountered in a longitudinal direction relative to the socket 30, an expanded fluoropolymer such as ePTFE with a fibril microstructure may have the fibrils oriented in the longitudinal direction—i.e., in the direction of wear or abrasion. This may be particularly advantageous in the example of a uniaxially oriented fibril microstructure. Additionally, a relatively more dense (e.g., less porous) microstructure may be employed to enhance overall wear and abrasion resistant of inner or outer layers of the socket 30. Abrasion and wear resistance of the socket 30 may be promoted via other additional or alternative features. For example, an abrasion resistant coating may be applied to an exterior or interior surface of the socket 30. One such coating may be a copolymer of Tetrafluoroethylene (TFE) and Perfluoromethylvinylether (PMVE). As another example of a wear/abrasion resistant coating, a hydrophilic and/or lubricious material may be employed, such as a hydrogel coating. These are just some examples, and other wear resistant features that may be employed in addition to, or as an alternative to abrasion-, or wear-resistant microstructures.

In view of at least the foregoing, various examples include the materials forming the socket 30 promoting tissue ingrowth (e.g., to reduce thrombosis or help secure the multicomponent implantable device 10 at a desired implant location). Additionally, in some implementations, materials forming the socket 30 include a film microstructure in which fibrillar orientation is in a direction substantially parallel the longitudinal axis of socket 30. Such a configuration can help ensure that longitudinal motion of one or more or each of the plurality of components 20 (e.g., anchor components, tether components, and/or tether lock components) will be aligned with the fibrillar orientation to help reduce friction and/or wear on the component(s).

In various examples, the socket 30 may be formed from a material set including ePTFE graft material, elastomer material, other polymeric material, or combinations of such materials. In some embodiments, the socket 30 is constructed from ePTFE stretch graft material, such as material similar to that available from W.L. Gore & Associates, Inc. under the trade name "GORE-TEX" brand "Stretch Vascular Grafts." The socket 30 may include material modified to enhance column strength (e.g., by including one or more layers of material that are relatively denser, or less porous). The socket 30 may also include materials that are partially or fully bio-resorbable or bio-absorbable. In such examples, the socket 30 can be configured to provide temporary fixation (e.g., between component(s) and or with the body) which degrades partially or fully over time.

In some embodiments, the socket 30 includes one or more layers configured as a mesh, or network of material, that is adapted to enhance biocompatibility and fibrosis following implantation. Such mesh or network may be formed by crossing strands of material, or by forming intermittent voids or openings in a layer of material. Such mesh or network configurations may be implemented to promote tissue growth onto and/or through the mesh or network surface. In some examples, tissue growth may be promoted by incorporating a relatively rough and/or porous outer and/or inner surface into the socket 30. If desired, one or more holes may be formed into or through the socket material, which may promote the formation of scar tissue fibrocytes (e.g., to promote strong fixation to tissue).

It should be understood that the other component(s) of the implantable device 10 may employ similar features to enhance wear or abrasion resistance of those components. For example, as previously referenced, the second component 24 may be configured as a tether component formed of a relatively flexible, elongate material (e.g., monofilament, multifilament, braided, or other material). Where abrasion is likely to be encountered in a longitudinal direction relative to the socket 30, an expanded fluoropolymer such as ePTFE with a fibril microstructure may have the fibrils oriented in the longitudinal direction—i.e., in the direction of wear or abrasion. Again, this may be particularly advantageous in the example of a uniaxially oriented fibril microstructure. Again, a relatively more dense (e.g., less porous) microstructure may be employed (e.g., a relatively more dense ePTFE or expanded (fluoro)polymer) to enhance overall wear and abrasion resistant of the second component 24.

Similarly to the socket 30, abrasion and wear resistance may also be promoted via other additional or alternative features. For example, an abrasion resistant coating may be applied to the second component 24. One such coating may be a copolymer of Tetrafluoroethylene (TFE) and Perfluoromethylvinylether (PMVE). As another example of a wear/abrasion resistant coating, a hydrophilic and/or lubricious material may be employed, such as a hydrogel coating. Again, these are just some examples, and other wear resistant features that may be employed in addition to, or as an alternative to abrasion-, or wear-resistant microstructures. It should also be understood that similar principals may be applied to the other components of the implantable device 10, such as the fourth component 28.

In some examples, one or more layer(s) of the socket 30 may be formed of a material having a desired permeability. For example, in some examples the socket includes one or more layers that are impermeable to cellular integration, or which are impermeable to body fluids such as blood or blood serum, to improve overall mechanical characteristics and/or biologic response as desired.

In some examples, the outermost layer(s) may have an internodal distance or spacing of greater than or equal to 6 micrometers.

In some examples, the outermost layer(s), or exposed surface layer(s), may be configured to achieve one or more tiers within a range of biologic, or foreign body responses.

A first tier of foreign body responses (e.g., at a first relative material porosity) would include impermeability to blood plasma and serum.

A second tier of foreign body responses (e.g., at a second relative material porosity) would include plasma and/or serum infiltration into the exposed surface.

A third tier of foreign body responses (e.g., at a third, higher relative material porosity) would include minimal, or some level of extracellular matrix integration.

A fourth tier of foreign body response (e.g., at a fourth, even higher relative material porosity) would include cellular integration.

A fifth tier of foreign body responses (e.g., at a fifth, highest relative material porosity) would include vascular integration, including full tissue ingrowth and blood vessels supplying the tissue. The outermost, or exposed surface(s) can be tailored to exhibit any of these relative tiers of foreign body responses as desired, for example by selecting material microstructure, coatings, and/or surface treatments.

An assessment of whether or not the material is exhibiting a particular tier of foreign body response may be made using a variety of techniques. Measurement techniques for assessing the presence of one or more tiers of foreign body response could include a permeability test such as those described according to ASTM standards. In various examples, a histology assessment may be an appropriate tool for assessing foreign body responses under any of the various tiers previously described.

The foreign body response of the outermost layer or surface may be additionally or alternatively tailored through the use of coatings and/or surface treatments. For example, the outermost layer(s) may be treated with heparin bonding (e.g., including that sold under the tradename "CBAS" by W.L. Gore & Associates, Inc. and Carmeda AB, which is a heparin bonding technology for lasting thromboresistance). As another example, the socket 30 may be tailored to include one or more eluting technologies, such as drug elution technologies. Any of a variety of biological coatings can be included on the outer and/or inner surfaces of the socket 30 to achieve a desired biologic response, including promoting healing and/or tissue growth, for example.

Figure 11:
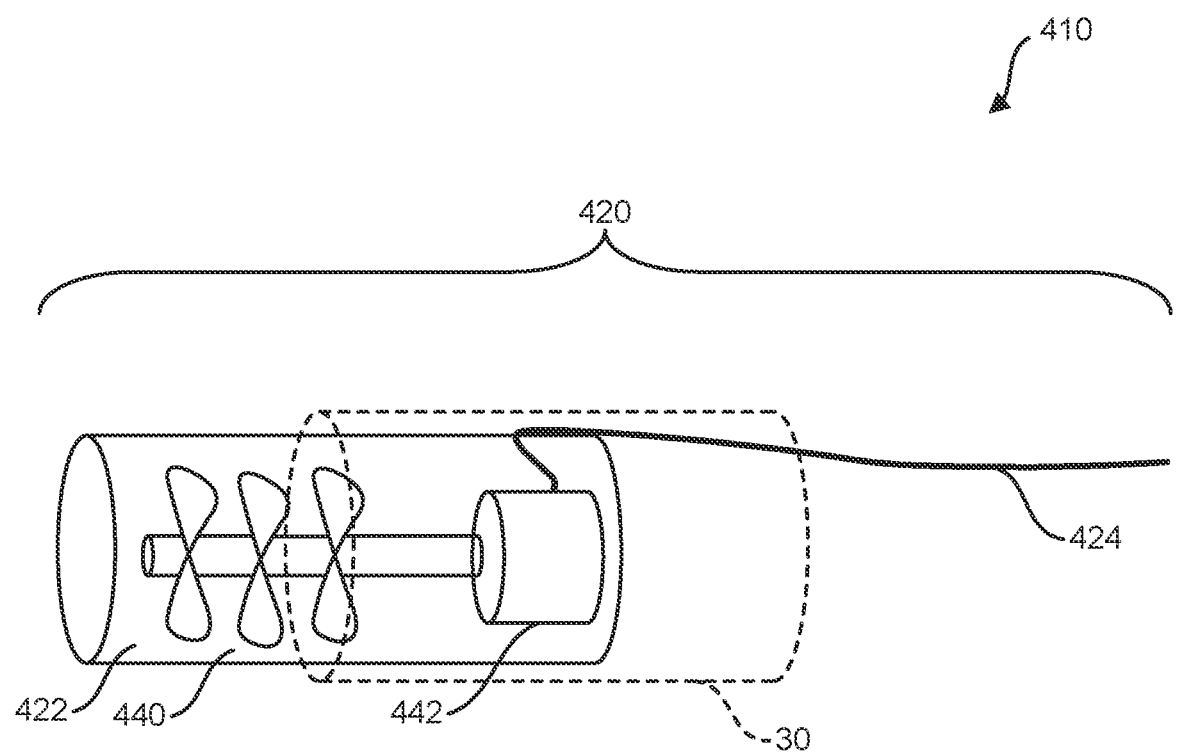
FIG. 11 shows an implantable device utilizing a socket, according to some examples.

As previously referenced, the socket 30 and any of the foregoing features and examples thereof may be applied in a variety of device contexts. For example, FIG. 11 shows another implantable device 410 utilizing the socket 30, according to some examples. As shown, the implantable device 410 includes a plurality of components 420, such as a first component 422, a second component 424, and socket 30 extending over the first component 422 and the second component 424. The socket 30 is again generally configured to enhance inter-component and/or inter-environment interactions of an implantable device. For ease of illustration and visualization of the underlying components, the socket 30 is again illustrated generically in a see-through manner, designated by broken lines.

The implantable device 410 in the example of FIG. 11 is an implantable blood pump, such as a left ventricular assist device (LVAD) configured for implantation in the body of a patient (not shown). As shown, the first component 422 is optionally a pump apparatus and the second component 424 is a lead (e.g., an electrical or mechanical connector) extending from the first component 422 (e.g., for powering or controlling the pump apparatus). The first component 422 includes a body 440 and an impeller and motor subassembly 442 housed, or maintained by the body 440. The implantable device 410 is shown generically in FIG. 11, and can be any of a variety of blood pump designs with any of a variety of components that would benefit from use of the socket 30. As shown, the socket 30 may assist with maintaining a physical position of the second component 424 relative to the first component 422 (e.g., to avoid unwanted flexing or movement at the interface between the first and second components 422, 424). The socket 30 may additionally or alternatively promote any of the inter-environment interactions mentioned in association with any of the other examples described herein (e.g., impermeability, reduced thrombosis, tissue ingrowth, prevention of tissue ingrowth, and combinations thereof, or others).

Various methods of treatment using the implantable devices of any of the preceding examples include delivering the implantable device to a location in a body of a patient (e.g., into a heart of a patient). In various examples, another component (e.g., the third component 26) is received in the socket 30 in vivo (e.g., by being slid into the socket 30 as part of a tensioning or other process in association with a transcatheter mitral chordal repair method).

Although the various examples above are cast in the context of an implantable device, the various concepts and features above may also be applied in the context of a single component as desired. For the avoidance of doubt, the scope of invention is not limited to multi-component implantable devices. Specifically, in some examples, the socket 30 may be implemented in association with a single component, and need not be configured to and/or actually receive any additional, discrete components. For example, the socket 30 can be used to help smooth, or reduce radial profile variability. Transverse elements of the component that protrude relative to a surrounding portion of the outer profile could result in thrombosis, or damage to surrounding tissue, for example.

Figure 12:
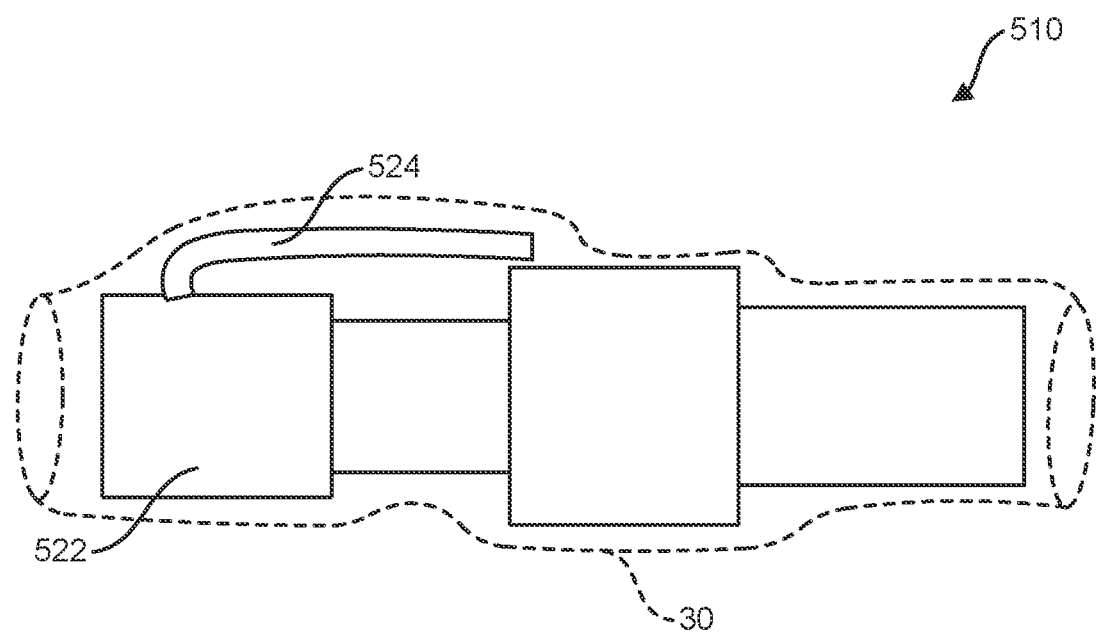
FIG. 12 shows an implantable device utilizing a socket, according to some examples.

FIG. 12 shows an implantable device 510 including a first component 522 having a first outer profile defining first radial variability along the first component. The first component 522 also includes an optional radial projection 524 that is integral to the first component (e.g., an integral anchor, antennae, or other feature) that projects transversely and defines a portion of the first outer profile and the associated radial variability of the first outer profile. The first component 522 could be an implantable sensor, a blood pump, or other device as desired. As shown, the implantable device 510 includes socket 30 extending over the first outer profile of the first component 524 to define a second outer profile having a second radial variability that is reduced relative to the first radial variability. In other words, the outer profile of the first component 524, including the optional, radial projection 524 has been smoothed out by the socket 30, such the radial variability of the first outer profile is reduced. Similarly to other examples, the socket 30 optionally includes one or more outer exposed surfaces configured to exhibit one or more tiers of foreign body responses within a range of possible foreign body responses.

Inventive concepts of this application have been described above both generically and with regard to specific embodiments/examples. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An implantable device comprising:
    a first component having a first outer profile defining first radial variability along the first component; and
    a socket extending over the first outer profile of the first component to define a second outer profile having a second radial variability that is reduced relative to the first radial variability, wherein the socket includes an outer portion supported by at least one reinforcing member, and an inner portion, wherein the at least one reinforcing member is coupled to the inner portion and is positioned between the inner portion and the outer portion such that an entirety of the at least one reinforcing member is embedded in the inner portion and the outer portion.

2. The implantable device of claim 1, wherein the inner portion includes a plurality of layers.

3. The implantable device of claim 1, wherein the inner portion is wrapped.

4. The implantable device of claim 1, wherein the at least one reinforcing member includes a continuous, helical pattern.

5. The implantable device of claim 1, wherein the at least one reinforcing member includes a plurality of discontinuous rings.

6. The implantable device of claim 1, wherein the at least one reinforcing member is elastically deformable.

7. The implantable device of claim 1, wherein the outer portion includes a plurality of layers.

8. The implantable device of claim 1, wherein the outer portion is wrapped.

9. The implantable device of claim 1, wherein the at least one reinforcing member is elastically deformable to an enlarged diameter from which the at least one reinforcing member elastically recovers.

10. The implantable device of claim 1, wherein the at least one reinforcing member is deformable from an enlarged diameter to a reduced diameter.

11. An implantable device comprising:
    a first component having a first outer profile defining first radial variability along the first component; and
    a socket extending over the first outer profile of the first component to define a second outer profile having a second radial variability that is reduced relative to the first radial variability, wherein the socket includes an inner portion coupled to at least one reinforcing member, and an outer portion, wherein the at least one reinforcing member is positioned between the inner portion and the outer portion, wherein the at least one reinforcing member is elastically deformable to an enlarged diameter from which the at least one reinforcing member elastically recovers.

12. The implantable device of claim 11, wherein the inner portion includes a plurality of layers.

13. The implantable device of claim 11, wherein the inner portion is wrapped.

14. The implantable device of claim 11, wherein the at least one reinforcing member includes a continuous, helical pattern.

15. The implantable device of claim 11, wherein the at least one reinforcing member includes a plurality of discontinuous rings.

16. The implantable device of claim 11, wherein the at least one reinforcing member is elastically deformable from the enlarged diameter to a reduced diameter.

* * * * *